United States Patent
Liu et al.

(10) Patent No.: US 11,090,268 B2
(45) Date of Patent: Aug. 17, 2021

(54) TARGETED HYDROPHOBIC ANTI-TUMOR DRUG NANOFORMULATION AND PREPARATION METHOD THEREOF

(71) Applicant: AC PHARMACEUTICALS CO., LTD, Guangzhou (CN)

(72) Inventors: Feng Liu, Guangzhou (CN); Shuting Lai, Guangzhou (CN); Fuchun Cao, Guangzhou (CN); Yang Zheng, Guangzhou (CN); Yuanfa Lian, Guangzhou (CN)

(73) Assignee: AC PHARMACEUTICALS CO., LTD, Guangzhou (CN)

( * ) Notice: Subject to any disclaimer, the term of this patent is extended or adjusted under 35 U.S.C. 154(b) by 401 days.

(21) Appl. No.: 16/060,103

(22) PCT Filed: Nov. 24, 2016

(86) PCT No.: PCT/CN2016/107127
§ 371 (c)(1),
(2) Date: Jun. 7, 2018

(87) PCT Pub. No.: WO2017/101653
PCT Pub. Date: Jun. 22, 2017

(65) Prior Publication Data
US 2020/0261368 A1 Aug. 20, 2020

(30) Foreign Application Priority Data

Dec. 14, 2015 (CN) .......................... 201510932623.7

(51) Int. Cl.
| | |
|---|---|
| *A61K 9/19* | (2006.01) |
| *A61K 9/51* | (2006.01) |
| *A61K 31/337* | (2006.01) |
| *A61K 31/436* | (2006.01) |
| *A61K 31/4745* | (2006.01) |
| *A61K 31/675* | (2006.01) |
| *A61K 31/704* | (2006.01) |
| *A61K 38/13* | (2006.01) |
| *A61K 38/14* | (2006.01) |

(52) U.S. Cl.
CPC .............. *A61K 9/19* (2013.01); *A61K 9/5161* (2013.01); *A61K 9/5169* (2013.01); *A61K 9/5192* (2013.01); *A61K 31/337* (2013.01); *A61K 31/436* (2013.01); *A61K 31/4745* (2013.01); *A61K 31/675* (2013.01); *A61K 31/704* (2013.01); *A61K 38/13* (2013.01); *A61K 38/14* (2013.01)

(58) Field of Classification Search
CPC .. A61K 31/337; A61K 31/436; A61K 9/5161; A61K 9/19; A61K 31/4745; A61K 31/675; A61K 9/5169; A61K 38/13; A61K 9/5192; A61K 38/14; A61K 31/704
See application file for complete search history.

(56) References Cited

U.S. PATENT DOCUMENTS

2010/0215751 A1    8/2010   Desai

FOREIGN PATENT DOCUMENTS

| | | |
|---|---|---|
| CN | 101537185 | 9/2009 |
| CN | 102327230 | 1/2012 |
| CN | 102688200 | 9/2012 |
| CN | 105412024 | 3/2016 |
| WO | 2015018380 | 2/2015 |

OTHER PUBLICATIONS

Martins et al. "Design of Novel BSA/hyaluronic Acid Nanodispersions for Transdermal Pharma Purposes" in Molecular Pharmacy, May 5, 2014, pp. 1478-1488.*
Liu et al., CN 102688200 A, 2012; Eng. Translation (Machine).*
Miele et al. ("Albumin-bound formulation of paclitaxel (Abraxane ABI-007) in the treatment of breast cancer," International Journal of Nanomedicine, 2009:4 99-105).*
International Search Report filed in PCT/CN2016/107127 dated Feb. 22, 2017.

* cited by examiner

*Primary Examiner* — Blessing M Fubara
(74) *Attorney, Agent, or Firm* — Rankin, Hill & Clark LLP

(57) ABSTRACT

The present invention relates to a targeted hydrophobic anti-tumor drug nanoformulation, which comprises a hydrophobic anti-tumor drug and a carrier with a mass ratio of 1:4-32.5, wherein the carrier is composed of 37.5-95.3 wt % albumin and 4.7-62.5 wt % hyaluronic acid-albumin conjugate, and the hyaluronic acid-albumin conjugate is prepared by albumin and hyaluronic acid with a molar ratio of 1:1-20. A preparation method of the nanoformulation comprises: preparing hyaluronic acid-albumin conjugate; formulating carrier solution; formulating drug solution; and preparing nanoformulation. The nanoformulation has even particle size distribution and good dispersibility, is stable without aggregating. The particle size of the lyophilized nanoformulation after being redissolved substantially remains unchanged, the yield of the nanoformulation is high and the efficacy is good after being filtered by a millipore filter (0.22 μm).

12 Claims, 2 Drawing Sheets

TARGETED HYDROPHOBIC ANTI-TUMOR DRUG NANOFORMULATION AND PREPARATION METHOD THEREOF

TECHNICAL FIELD

The present invention belongs to the field of drugs, and more particularly, to a targeted hydrophobic anti-tumor drug nanoformulation and a preparation method thereof.

BACKGROUND

Blood vessels in most tumors grow rapidly and irregularly, interior lymphatic systems are slowly eliminated, and have a tumor permeability enhancement factor, so that macromolecules and nanoparticles are easy to stay in the tumor, which is called Enhanced Permeability and Retention (EPR). A nano-drug delivery system can be passively targeted to the tumor due to the EPR, and has been paid more and more attention in the application process of targeted tumor therapy. Ordinary nanoformulations, such as liposomes or nanoparticles, will be recognized by a human reticuloendothelial system in the plasma, so that the plasma clearance of the nanoformulation is accelerated, and the therapeutic effect is reduced. Therefore, the surface-modified nanoformulations have drawn extensive study and attention of people.

The albumin is a protein that is abundant in the plasma. Common albumins in drug carrier studies include human serum albumins, bovine serum albumins and egg albumins. There are many drug binding sites in albumin molecules, which can effectively load different kinds of drugs; and meanwhile, the albumin has the features of high water solubility, good stability and degradability, has high biocompatibility, and has been approved by US Food and Drug Administration (FDA) for use in the human body. Therefore, the albumin is an ideal carrier for drug delivery. Meanwhile, amino groups, sulfydryl, and the like, present on the albumin can be further modified with active targeting groups to increase the targeting property. The listing of the existing paclitaxel (protein-bound particles) for injectable suspension (Abraxane®) has attracted widespread market attention.

Patent CN201210142991 prepares a hyaluronic acid-human albumin conjugate as a carrier, and then obtains a plant-based anti-cancer targeted nanoformulation by placing the carrier with a plant-based anti-cancer drug and a nanoparticle stabilizer under the condition of high-speed homogenization, high-pressure homogenization or ultrasound treatment. The nanoformulation has a biological targeting effect on tumor cell surface receptors, such as CD44 after the nanoformulation is injected into the human body, the drug is accumulated at the tumor site based on the EPR effect of the tumor and the high binding of HA to the CD44, and the cycle time of the nano-drug delivery system in the human body is prolonged.

In biomedical applications, the particle size of the nanoparticle drug is relatively important, different particle sizes are corresponding to different metabolism paths, the nanoparticle drug with a small particle size is metabolized through a kidney, while the nanoparticle drug with a large particle size is metabolized through a liver. 20-200 nm particles have a passive targeting effect on the tumor, the nanoparticle drug in the scope of the particle size can eliminate some biomedical effects caused by the size of the drug itself, thus increasing the therapeutic effect.

The injection is one kind of sterile preparations, and the sterility of the injection is realized through well-controlled and validated sterilization/degerming production processes and strict implementation of Good Manufacturing Practice for Pharmaceutical Products (GMP) in the production process. Preparations containing a lot of proteins (such as albumins) cannot be sterilized by a regular method (such as high temperature) because high temperature can cause albuminous degeneration. A filtration sterilization method is a final sterilization method recognized by a regulatory authority for products that have instability, so that the conditions including high-temperature sterilization cannot be used. Therefore, the filtration sterilization through a 0.22 µm filter is a preferred solution for preparing the injection nanoformulation.

However, the nanoformulation particles of CN201210142991 have a larger particle size distribution coefficient and a wider particle size distribution; after being lyophilized and redissolved, since the hyaluronic acid molecular chains for modifying the human serum albumins are twined to cause mutual aggregation and adhesion of the particles, which increases the particle size of the lyophilized product after being redissolved. Therefore, ducts of a filter membrane of the filter are easily blocked when conducting filtration by a millipore filter (0.22 µm), which reduces the particle concentration in the filtrate, thus reducing the content of the drug in the filtrate, and affecting the drug effect and reducing the yield of the product.

SUMMARY

Based on this, one of the objectives of the present invention is to provide a targeted hydrophobic anti-tumor drug nanoformulation. The nanoformulation has even particle size distribution and good dispersibility, is stable without aggregating. The particle size of the lyophilized nanoformulation after being redissolved substantially remains unchanged; and the drug concentration in the filtered solution is basically unchanged after being filtered by a millipore filter (0.22 µm).

A specific technical solution to achieve the objectives above is as follows.

A targeted hydrophobic anti-tumor drug nanoformulation comprises a hydrophobic anti-tumor drug and a carrier with a mass ratio of 1:4-32.5, wherein the carrier is composed of 37.5-95.3 wt % albumin and 4.7-62.5 wt % hyaluronic acid-albumin conjugate, and the hyaluronic acid-albumin conjugate is prepared by albumin and hyaluronic acid with a molar ratio of 1:1-20.

In some of the embodiments, the targeted hydrophobic anti-tumor drug nanoformulation comprises a hydrophobic anti-tumor drug and a carrier with a mass ratio of 1:4.8-19, wherein the carrier is composed of 50.0-95.0 wt % albumin and 5.0-50.0 wt % hyaluronic acid-albumin conjugate, and the hyaluronic acid-albumin conjugate is prepared by albumin and hyaluronic acid with a molar ratio of 1:2-20.

In some of the embodiments, the molecular weight of the hyaluronic acid is 2-60 kDa.

In some of the embodiments, the albumin is selected from human serum albumin, bovine serum albumin, egg albumin and recombinant human serum albumin.

In some of the embodiments, the hydrophobic anti-tumor drug is selected from taxol, docetaxel, aziditaxel, adriamycin, camptothecin, cyclosporin, rapamycin, vancomycin, thiotepa or their derivatives thereof.

In some of the embodiments, the targeted hydrophobic anti-tumor drug nanoformulation further comprises a nanoparticle stabilizer, wherein the nanoparticle stabilizer is selected from a polyoxyethylene-polypropylene oxide-polyoxyethylene block polymer, d-α-tocopheryl polyethylene glycol succinateand povidone, and the nanoparticle stabilizer is 1.0-10.0% of the mass of the hydrophobic anti-tumor drug.

Another objective of the present invention is to provide a preparation method of the targeted hydrophobic anti-tumor drug nanoformulation.

A specific technical solution is as follows.

The preparation method of the targeted hydrophobic anti-tumor drug nanoformulation above comprises the following steps of:

(1) preparing hyaluronic acid-albumin conjugate:
  adding hyaluronic acid and albumin into an aqueous medium for dissolution, adjusting a solution pH to 5.0-6.0, adding N-(3-Dimethylaminopropyl)-N'-ethylcarbodiimide hydrochloride and N-hydroxysulfosuccinimide sodium salt into the above solution for reaction for 15-60 min, then adjusting the solution pH to 7.0-7.5, continuously stirring at room temperature for reaction for 3-24h, dialyzing and removing unbound hyaluronic acid, unreacted N-(3-Dimethylaminopropyl)-N'-ethylcarbodiimide hydrochloride, N-hydroxysulfosuccinimide sodium salt and other by-products after the reaction is finished, and obtaining the hyaluronic acid-albumin conjugate after being lyophilized; or
  dissolving the hyaluronic acid into an aqueous medium, adjusting a solution pH to 5.0-6.0, adding N-(3-Dimethylaminopropyl)-N'-ethylcarbodiimide hydrochloride and N-hydroxysulfosuccinimide sodium salt, stirring at room temperature for reaction for 15-60 min to obtain hyaluronic acid succinimide active eester; and then adding the hyaluronic acid succinimide active ester drop by drop into an albumin aqueous solution or adding the albumin aqueous solution drop by drop into the hyaluronic acid succinimide active ester, adjusting a solution pH to 7.0-7.5, stirring at room temperature for reaction for 3-24 h, dialyzing and removing unbound hyaluronic acid, unreacted N-(3-Dimethylaminopropyl)-N'-ethylcarbodiimide hydrochloride, N-hydroxysulfosuccinimide sodium salt and other by-products after the reaction is finished, and obtaining the hyaluronic acid-albumin conjugate after being lyophilized;

(2) formulating carrier solution:
  dissolving the albumin and the hyaluronic acid-albumin conjugate prepared in step (1) into an aqueous medium to obtain a carrier solution;

(3) formulating drug solution:
  dissolving a hydrophobic anti-tumor drug, or a hydrophobic anti-tumor drug and a nanoparticle stabilizer into an organic solvent to obtain a drug solution; and (4) preparing nanoformulation:
  adding the drug solution prepared in (3) into the carrier solution prepared in step (2) under a homogeneous condition to obtain initial emulsion, obtaining multiple emulsion under high-pressure homogenization condition, then removing the organic solvent, filtering, and lyophilizing to obtain the targeted hydrophobic anti-tumor drug nanoformulation.

In some of the embodiments, the concentration of the carrier in the carrier solution according to step (2) is 4.0-50.0 mg/mL, and the concentration of the hydrophobic anti-tumor drug in the drug solution according to step (3) is 16.0-345.0 mg/mL.

In some of the embodiments, the aqueous medium according to step (1) is 2-(N-morpholine)ethanesulfonic acid buffer, phosphate buffer or sterile water; the aqueous medium according to step (2) is sterile water, phosphate buffer, normal saline, 5.0 wt % aqueous glucose solution or 5.0 wt % mannitol solution; and the organic solvent according to step (3) is dichloromethane, chloroform, a mixture of dichloromethane and ethyl alcohol, or a mixture of chloroform and ethyl alcohol.

In some of the embodiments, the pressure of the high-pressure homogenization condition according to step (4) is 10000-40000 psi, the material flow of the high-pressure homogenization condition is 10.0-25.0 L/h, and the cycle index of the high-pressure homogenization condition is 7-20; and the method of removing the organic solvent is to remove the organic solvent by reduced pressure and rotary evaporation under a condition of 15.0-45.0□.

It has been found by the inventor of the present invention in the long-term accumulation of experience and experiments that adding unmodified albumin in the hyaluronic acid-albumin conjugate can reduce the particle size of the targeted hydrophobic anti-tumor drug nanoformulation according to the present invention, so that the particle size is more evenly distributed, which can avoid the mutual aggregation and adhesion of the particles. Therefore, the targeted hydrophobic anti-tumor drug nanoformulation described in the present invention has the following advantages.

1. The particle size distribution of the nanoformulation of the present invention is even and the majority is smaller than 220 nm, the particle size is not increased after the particle is redissolved and has a high yield after the particle is filtered by a millipore filter (0.22 μm), which greatly reduces the loss caused by the nanoformulation held back due to an overlarge particle size, thus increasing the drug effect, and strengthening the inhibiting effect on tumors.

2. Most particle sizes of the nanoformulation of the present invention are smaller than 220 nm, and the particle size is not increased after the nanoparticle is redissolved, which is beneficial for the nanoparticle to cycle for a long time in the body circulation system without being phagocytized by mononuclear macrophages and held back by the reticular system in the liver; the nanoformulation has an active targeting property, which is beneficial for guaranteeing sufficient plasma concentration of the targeted part, increasing the drug effect, and reducing the toxicity to nontumorous part.

3. The nanoformulation of the present invention after being redissolved has good stability in the solution, and is stable in an internal environment; moreover, the carrier and the drug can be kept into a stable complex in the delivery process.

BRIEF DESCRIPTION OF THE DRAWINGS

FIG. 2 is a comparison diagram of an inhibiting effect of targeted nanoformulations on tumors according to embodiments 1 to 2, embodiments 5 to 6 and references 1 to 2.

DETAILED DESCRIPTION

Figure 1:
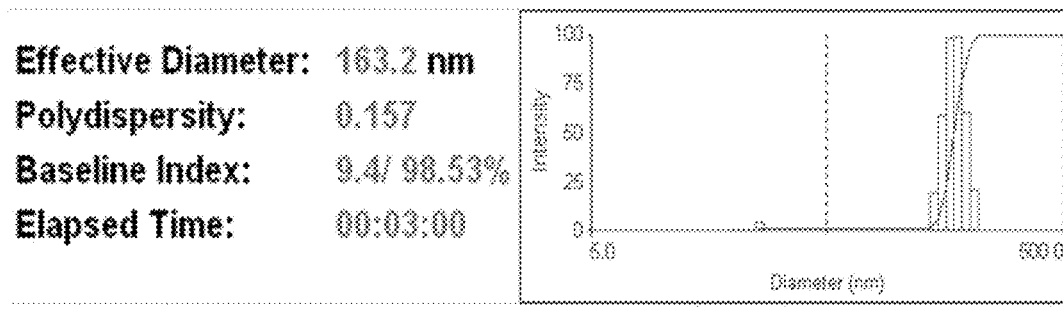
FIG. 1 is a particle size distribution diagram of a targeted nanoformulation particle before being filtered according to an embodiment 3.

The present invention is further described with reference to the embodiments hereinafter.

EDCI: N-(3-Dimethylaminopropyl)-N'-ethylcarbodiimide hydrochloride
Sulfo-NHS: N-hydroxysulfosuccinimide sodium salt
MES: 2-(N-morpholino)ethanesulfonic acid buffer
PEO-PPO-PEO block polymer: polyoxyethylene-polypropylene oxide-polyoxyethylene block polymer
TPGS: d-α-tocopheryl polyethylene glycol succinate
PVP: povidone

EMBODIMENT 1

Preparation of Taxol Targeted Anti-Tumor Nanoformulation (1) Preparing hyaluronic acid-albumin conjugate:
2.7042 g hyaluronic acid (molecular weight 2 kDa) and 4.4958 g human albumin (1/20 times of the hyaluronic acid in mole) were added into 27.0 mL sterile water for dissolution, a solution pH was adjusted to 5.5, then 12.9600 g EDCI and 29.3584 g Sulfo-NHS were added into the above solution for reaction for 15 min, then the solution pH was adjusted to 7.4, the solution was continuously stirred at room temperature for reaction for 5 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:
0.9720 g human serum albumin and 0.1080 g hyaluronic acid-albumin conjugate were dissolved in 216.0 mL sterile water to obtain a carrier solution;

(3) formulating drug solution:
0.1200 g taxol was dissolved in 2.7 mL mixed solvent (9:1) of chloroform and ethyl alcohol to obtain a drug solution;

(4) preparing nanoformulation:
the drug solution prepared in step (3) was added into the carrier solution prepared in step (2) under a high-speed homogenization condition to obtain initial emulsion, multiple emulsion was obtained through circulating for 7 times under high-pressure homogenization condition (pressure: 20000 psi, material flow: 10.0 L/h), then the organic solvent was removed by reduced pressure and rotary evaporation under a condition of 30.0-45.0☐, the mixture was filtered by a 0.22 μm filter, and then the filtrate was lyophilized to obtain the taxol targeted anti-tumor nanoformulation.

EMBODIMENT 2

Preparation of Taxol Targeted Anti-Tumor Nanoformulation (1) Preparing hyaluronic acid-albumin conjugate:
2.4575 g hyaluronic acid (molecular weight 3 kDa) and 8.1711 g human serum albumin (3/20 times of the hyaluronic acid in mole) were added into 27.0 mL 0.01M MES solution for dissolution, a solution pH was adjusted to 5.5, then 6.2813 g EDCI and 14.2291 g Sulfo-NHS were added into the above solution for reaction for 15 min, then the solution pH was adjusted to 7.4, the solution was continuously stirred at room temperature for reaction for 4 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:
1.2754 g human serum albumin and 0.3189 g hyaluronic acid-albumin conjugate were dissolved in 213.0 mL sterile water to obtain a carrier solution;

(3) formulating drug solution:
0.1200 g taxol was dissolved in 7.1 mL mixed solvent (9:1) of chloroform and ethyl alcohol to obtain a drug solution;

(4) preparing nanoformulation:
the drug solution prepared in step (3) was added into the carrier solution prepared in step (2) under a high-speed homogenization condition to obtain initial emulsion, multiple emulsion was obtained through circulating for 10 times under high-pressure homogenization condition (pressure: 14000 psi, material flow: 12.0 L/h), then the organic solvent was removed by reduced pressure and rotary evaporation under a condition of 15.0-25.0☐ and −0.1 MPa, the mixture was filtered by a 0.22 μm filter, and then the filtrate was lyophilized to obtain the taxol targeted anti-tumor nanoformulation.

EMBODIMENT 3

Preparation of Taxol Targeted Anti-Tumor Nanoformulation (1) Preparing hyaluronic acid-albumin conjugate:
1.4319 g hyaluronic acid (molecular weight 5 kDa) and 3.1741 g human serum albumin (1/6 times of the hyaluronic acid in mole) were added into 18.0 mL 0.01M PBS for dissolution, a solution pH was adjusted to 5.4, then 1.6470 g EDCI and 3.3579 g Sulfo-NHS were added into the above solution for reaction for 15 min, then the solution pH was adjusted to 7.5, the solution was continuously stirred at room temperature for reaction for 4 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:
1.0594 g human serum albumin and 0.4606 g hyaluronic acid-albumin conjugate were dissolved in 150.0 mL sterile water to obtain a carrier solution;

(3) formulating drug solution:
0.0800 g taxol was dissolved in 4.3 mL mixed solvent (9:1) of chloroform and ethyl alcohol to obtain a drug solution;

(4) preparing nanoformulation:
the drug solution prepared in step (3) was added into the carrier solution prepared in step (2) under a high-speed homogenization condition to obtain initial emulsion, multiple emulsion was obtained through circulating for 12 times under high-pressure homogenization condition (pressure: 17000 psi, material flow: 15.0 L/h), then the organic solvent was removed by reduced pressure and rotary evaporation under a condition of 15.0-25.0☐ and −0.1 Mpa, the mixture was filtered by a 0.22 μm filter, and then the filtrate was lyophilized to obtain the taxol targeted anti-tumor nanoformulation.

EMBODIMENT 4

Preparation of Aziditaxel Targeted Anti-Tumor Nanoformulation (1) Preparing hyaluronic acid-albumin conjugate:

1.6884 g hyaluronic acid (molecular weight 8 kDa) and 2.6316 g human serum albumin (3/16 times of the hyaluronic acid in mole) were added into 24.0 mL 0.01M MES for dissolution, a solution pH was adjusted to 5.6, then 1.0115 g EDCI and 2.0622 g Sulfo-NHS were added into the above solution for reaction for 15 min, then the solution pH was adjusted to 7.4, the solution was continuously stirred at room temperature for reaction for 4 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:

2.16 g human serum albumin and 1.44 g hyaluronic acid-albumin conjugate were dissolved in 290.0 mL sterile water to obtain a carrier solution;

(3) formulating drug solution:

0.4000 g aziditaxel was dissolved in 7.2 mL mixed solvent (9:1) of chloroform and ethyl alcohol to obtain a drug solution;

(4) preparing nanoformulation:

the drug solution prepared in step (3) was added into the carrier solution prepared in step (2) under a high-speed homogenization condition to obtain initial emulsion, multiple emulsion was obtained through circulating for 14 times under high-pressure homogenization condition (pressure: 20000 psi, material flow: 15.0 L/h), then the organic solvent was removed by reduced pressure and rotary evaporation under a condition of 15.0-25.0☐ and −0.1 Mpa, the mixture was filtered by a 0.22 μm filter, and then the filtrate was lyophilized to obtain the taxol targeted anti-tumor nanoformulation.

EMBODIMENT 5

Preparation of Taxol Targeted Anti-Tumor Nanoformulation (1) Preparing hyaluronic acid-albumin conjugate:

1.8144 g hyaluronic acid (molecular weight 10 kDa) and 2.5856 g human serum albumin (3/14 times of the hyaluronic acid in mole) were added into 30.0 mL 0.01M PBS for dissolution, a solution pH was adjusted to 5.3, then 0.8696 g EDCI and 1.4774 g Sulfo-NHS were added into the above solution for reaction for 15 min, then the solution pH was adjusted to 7.4, the solution was continuously stirred at room temperature for reaction for 6 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:

4.1800 g human serum albumin and 0.2200 g hyaluronic acid-albumin conjugate were dissolved in 300.0 mL sterile water to obtain a carrier solution;

(3) formulating drug solution:

0.6000 g taxol was dissolved in 7.3 mL mixed solvent (9:1) of chloroform and ethyl alcohol to obtain a drug solution;

(4) preparing nanoformulation:

the drug solution prepared in step (3) was added into the carrier solution prepared in step (2) under a high-speed homogenization condition to obtain initial emulsion, multiple emulsion was obtained through circulating for 10 times under high-pressure homogenization condition (pressure: 25000 psi, material flow: 15.0 L/h), then the organic solvent was removed by reduced pressure and rotary evaporation under a condition of 15.0-25.0☐ and −0.1 Mpa, the mixture was filtered by a 0.22 μm filter, and then the filtrate was lyophilized to obtain the taxol targeted anti-tumor nanoformulation.

EMBODIMENT 6

Preparation of Taxol Targeted Anti-Tumor Nanoformulation (1) Preparing hyaluronic acid-albumin conjugate:

1.6289 g hyaluronic acid (molecular weight 15 kDa) and 1.8054 g human serum albumin (¼ times of the hyaluronic acid in mole) were added into 33.0 mL 0.01M MES for dissolution, a solution pH was adjusted to 5.5, then 0.4164 g EDCI and 0.7074 g Sulfo-NHS were added into the above solution for reaction for 20 min, then the solution pH was adjusted to 7.3, the solution was continuously stirred at room temperature for reaction for 3 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:

3.8465 g human serum albumin and 0.6869 g hyaluronic acid-albumin conjugate were dissolved in 230.0 mL sterile water to obtain a carrier solution;

(3) formulating drug solution:

0.8000 g taxol was dissolved in 5.0 mL mixed solvent (9:1) of chloroform and ethyl alcohol to obtain a drug solution;

(4) preparing nanoformulation:

the drug solution prepared in step (3) was added into the carrier solution prepared in step (2) under a high-speed homogenization condition to obtain initial emulsion, multiple emulsion was obtained through circulating for 12 times under high-pressure homogenization condition (pressure: 30000 psi, material flow: 18.0 L/h), then the organic solvent was removed by reduced pressure and rotary evaporation under a condition of 15.0-25.0☐ and −0.1 MPa, the mixture was filtered by a 0.22 μm filter, and then the filtrate was lyophilized to obtain the aziditaxel targeted anti-tumor nanoformulation.

EMBODIMENT 7

Preparation of Docetaxel Targeted Anti-Tumor Nanoformulation (1) Preparing hyaluronic acid-albumin conjugate:

1.2221 g hyaluronic acid (molecular weight 20 kDa) and 1.2191 g human serum albumin (3/10 times of the hyaluronic acid in mole) were added into 31.0 mL 0.01M PBS for dissolution, a solution pH was adjusted to 5.0, then 0.2343 g EDCI and 0.3184 g Sulfo-NHS were added into the above solution for reaction for 20 min, then the solution pH was adjusted to 7.0, the solution was continuously stirred at room temperature for reaction for 8 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:

3.7664 g human serum albumin and 2.0924 g hyaluronic acid-albumin conjugate were dissolved in 235.0 mL sterile water to obtain a carrier solution;

(3) formulating drug solution:

1.2000 g docetaxel was dissolved in 4.7 mL mixed solvent (9:1) of chloroform and ethyl alcohol to obtain a drug solution;

(4) preparing nanoformulation:

the drug solution prepared in step (3) was added into the carrier solution prepared in step (2) under a high-speed homogenization condition to obtain initial emulsion, multiple emulsion was obtained through circulating for 14 times under high-pressure homogenization condition (pressure: 25000 psi, material flow: 20.0 L/h), then the organic solvent was removed by reduced pressure and rotary evaporation under a condition of 15.0-25.0☐ and −0.1 Mpa, the mixture was filtered by a 0.22 μm filter, and then the filtrate was lyophilized to obtain the docetaxel targeted anti-tumor nanoformulation.

EMBODIMENT 8

Preparation of Camptothecin Targeted Anti-Tumor Nanoformulation (1) Preparing hyaluronic acid-albumin conjugate:

2.4475 g hyaluronic acid (molecular weight 25 kDa) was completely dissolved in 82.0 mL 0.01M MES, a solution pH was adjusted to 6.0, then 0.3003 g EDCI and 0.3401 g Sulfo-NHS were added into the above solution for reaction for 60 min to obtain hyaluronic acid succinimide active ester; and then the hyaluronic acid succinimide active ester was dropwise added into MES solution (2.4414 g/49.0 mL) of the human serum albumin (⅜ times of the hyaluronic acid in mole), the solution pH was adjusted to 7.5, the solution was continuously stirred at room temperature for reaction for 10 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:

3.5556 g human serum albumin and 4.4444 g hyaluronic acid-albumin conjugate were dissolved in 270.0 mL sterile water to obtain a carrier solution;

(3) formulating drug solution:

2.0000 g camptothecin was dissolved in 13.3 mL mixed solvent (11:1) of chloroform and ethyl alcohol to obtain a drug solution;

(4) preparing nanoformulation:

the drug solution prepared in step (3) was added into the carrier solution prepared in step (2) under a high-speed homogenization condition to obtain initial emulsion, multiple emulsion was obtained through circulating for 15 times under high-pressure homogenization condition (pressure: 30000 psi, material flow: 23.0 L/h), then the organic solvent was removed by reduced pressure and rotary evaporation under a condition of 15.0-25.0☐ and −0.1 MPa, the mixture was filtered by a 0.22 μm filter, and then the filtrate was lyophilized to obtain the camptothecin targeted anti-tumor nanoformulation.

EMBODIMENT 9

Preparation of Taxol Targeted Anti-Tumor Nanoformulation (1) Preparing hyaluronic acid-albumin conjugate:

1.3518 g hyaluronic acid (molecular weight 30 kDa) was completely dissolved in 68.0 mL 0.01M PBS, a solution pH was adjusted to 5.9, then 0.1037 g EDCI and 0.1174 g Sulfo-NHS were added into the above solution for reaction for 30 min to obtain hyaluronic acid succinimide active ester; and then PBS solution (1.4982 g/25.0 mL) of the human serum albumin (½ times of the hyaluronic acid in mole) was dropwise added into the hyaluronic acid succinimide active ester, the solution pH was adjusted to 7.5, the solution was continuously stirred at room temperature for reaction for 12 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:

5.7000 g human serum albumin and 1.9000 g hyaluronic acid-albumin conjugate were dissolved in 220.0 mL 0.01M PBS to obtain a carrier solution;

(3) formulating drug solution:

0.4000 g taxol and 0.0040 g PEO-PPO-PEO block polymer were dissolved in 3.3 mL chloroform to obtain a drug solution;

(4) preparing nanoformulation:

the drug solution prepared in step (3) was added into the carrier solution prepared in step (2) under a high-speed homogenization condition to obtain initial emulsion, multiple emulsion was obtained through circulating for 16 times under high-pressure homogenization condition (pressure: 25000 psi, material flow: 25.0 L/h), then the organic solvent was removed by reduced pressure and rotary evaporation under a condition of 15.0-25.0☐ and −0.1 Mpa, the mixture was filtered by a 0.22 μm filter, and then the filtrate was lyophilized to obtain the taxol targeted anti-tumor nanoformulation.

EMBODIMENT 10

Preparation of Thiotepa Targeted Anti-Tumor Nanoformulation (1) Preparing hyaluronic acid-albumin conjugate:

6.60701 g hyaluronic acid (molecular weight 40 kDa) was completely dissolved in 300.0 mL 0.01M MES, a solution pH was adjusted to 5.1, then 0.2327 g EDCI and 0.1845 g Sulfo-NHS were added into the above solution for reaction for 45 min to obtain hyaluronic acid succinimide active ester; and then the hyaluronic acid succinimide active ester was dropwise added into MES solution (6.0549 g/86.0 mL) of the recombinant human serum albumin (⅗ times of the hyaluronic acid in mole), the solution pH was adjusted to 7.2, the solution was continuously stirred at room temperature for reaction for 15 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:

4.8500 g recombinant human serum albumin and 8.0833 g hyaluronic acid-albumin conjugate were dissolved in 320.0 mL normal saline to obtain a carrier solution;

(3) formulating drug solution:

0.4000 g thiotepa and 0.0120 g TPGS were dissolved in 5.9 mL mixed solvent (7:1) of chloroform and ethyl alcohol to obtain a drug solution;

(4) preparing nanoformulation:

the drug solution prepared in step (3) was added into the carrier solution prepared in step (2) under a high-speed homogenization condition to obtain initial emulsion, multiple emulsion was obtained through circulating for 18 times under high-pressure homogenization condition (pressure: 10000 psi, material flow: 20.0 L/h), then the organic solvent was removed by reduced pressure and rotary evaporation under a condition of 15.0-25.0□ and −0.1 Mpa, the mixture was filtered by a 0.45 μm filter, and then the filtrate was lyophilized to obtain the thiotepa targeted anti-tumor nanoformulation.

EMBODIMENT 11

Preparation of Vancomycin Targeted Anti-Tumor Nanoformulation (1) Preparing hyaluronic acid-albumin conjugate:

5.4054 g hyaluronic acid (molecular weight 50 kDa) was completely dissolved in 540.0 mL 0.01M PBS, a solution pH was adjusted to 5.6, then 0.0829 g EDCI and 0.0282 g Sulfo-NHS were added into the above solution for reaction for 40 min to obtain hyaluronic acid succinimide active ester; and then egg albumin (3/8 times of the hyaluronic acid in mole) and PBS solution (3.5946 g/45.0 mL) were dropwise added into the hyaluronic acid succinimide active ester, the solution pH was adjusted to 7.4, the solution was continuously stirred at room temperature for reaction for 18 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:

5.4000 g egg albumin and 5.4000 g hyaluronic acid-albumin conjugate were dissolved in 240.0 mL 5.0 wt % aqueous glucose solution to obtain a carrier solution;

(3) formulating drug solution:

1.2000 g vancomycin and 0.0840 g TPGS were dissolved in 4.0 mL mixed solvent (15:1) of chloroform and ethyl alcohol to obtain a drug solution;

(4) preparing nanoformulation:

the drug solution prepared in step (3) was added into the carrier solution prepared in step (2) under a high-speed homogenization condition to obtain initial emulsion, multiple emulsion was obtained through circulating for 19 times under high-pressure homogenization condition (pressure: 35000 psi, material flow: 18.0 L/h), then the organic solvent was removed by reduced pressure and rotary evaporation under a condition of 15.0-25.0□ and −0.1 Mpa, the mixture was filtered by a 0.22 μm filter, and then the filtrate was lyophilized to obtain the vancomycin targeted anti-tumor nanoformulation.

EMBODIMENT 12

Preparation of Adriamycin Targeted Anti-Tumor Nanoformulation (1) Preparing hyaluronic acid-albumin conjugate:

0.3313 g hyaluronic acid (molecular weight 60 kDa) and 0.3671 g bovine serum albumin (double of the hyaluronic acid in mole) were added into 33.0 mL 0.01M MES for dissolution, a solution pH was adjusted to 5.4, then EDCI and Sulfo-NHS equal to the mole ratio of hyaluronic acid were added into the above solution for reaction for 15 min, then the solution pH was adjusted to 7.3, the solution was continuously stirred at room temperature for reaction for 24 h, unbound hyaluronic acid, unreacted EDCI, Sulfo-NHS and other by-products were dialyzed and removed after the reaction was finished, and the hyaluronic acid-albumin conjugate was obtained after being lyophilized;

(2) formulating carrier solution:

13.9683 g bovine serum albumin and 0.6984 g hyaluronic acid-albumin conjugate were dissolved in 300.0 mL 5.0 wt % mannitol solution to obtain a carrier solution;

(3) formulating drug solution:

2.0000 g adriamycin and 0.2000 g PVP were dissolved in 5.8 mL mixed solvent (5:1) of chloroform and ethyl alcohol to obtain a drug solution;

(4) preparing nanoformulation:

the drug solution prepared in step (3) was added into the carrier solution prepared in step (2) under a high-speed homogenization condition to obtain initial emulsion, multiple emulsion was obtained through circulating for 20 times under high-pressure homogenization condition (pressure: 40000 psi, material flow: 15.0 L/h), then the organic solvent was removed by reduced pressure and rotary evaporation under a condition of 15.0-25.0□ and −0.1 Mpa, the mixture was filtered by a 0.45 μm filter, and then the filtrate was lyophilized to obtain the adriamycin targeted anti-tumor nanoformulation.

Reference 1: Preparing Taxol Targeted Anti-Tumor Nanoformulation

The preparation was conducted in accordance with the embodiment 3 of patent CN201210142991:

(1) Preparing hyaluronic acid-albumin conjugate:

hyaluronic acid active ester was prepared firstly: 400 mg hyaluronic acid (molecular weight 5 kDa) was dissolved in 10.0 mL 0.1M MES buffer, and EDCI that was 1.2 times of the hyaluronic acid in mole and Sulfo-NHS that was 1.2 times of the hyaluronic acid in mole were added and stirred at room temperature for reaction for 30 min to obtain hyaluronic acid succinimide active ester; 500.0 mg human serum albumin lyophilized powder was dissolved in 10.0 mL sterile water and then added into the hyaluronic acid succinimide active ester; a pH value was adjusted to 7.0-7.2, and the mixture was stirred at room temperature for reaction for 60 min; then the mixture was added into a dialysis bag with a molecular weight up to 10000 after the reaction was finished, and unreacted reagent and reaction by-product were removed through dialysis; the hyaluronic acid-albumin solution after dialysis was lyophilized, and the lyophilized hyaluronic acid-albumin was dissolved in phosphate buffer (PBS buffer) with a pH of 5.5 to obtain albumin/hyaluronic acid solution;

(2) preparing taxol solution 50.0 mg taxol and 50.0 mg TPGS were dissolved in 1.0 mL chloroform to obtain the taxol solution;

(3) preparing taxol/TPGS/hyaluronic acid-albumin nanoformulation the taxol solution was added into the albumin/hyaluronic acid solution under a stirring condition to form initial emulsion; the initial emulsion was processed by a high-pressure homogenizer (9000-40000 psi) to obtain nanometre emulsion, the nanometre emulsion was transferred to a rotary evaporator to quickly remove organic solvent through reduced pressure and evaporation at 30.0-45.0□, and the remaining was lyophilized under an aseptic condition to obtain lyophilized powder.

Reference 2: Preparing Taxol Targeted Anti-Tumor Nanoformulation

The preparation was conducted in accordance with the embodiment 14 of patent CN201210142991:

(1) Preparing hyaluronic acid-albumin conjugate:

hyaluronic acid active ester was prepared firstly: 400.0 mg hyaluronic acid (molecular weight 5 kDa) was dissolved in 10.0 mL 0.1M MES buffer, and EDCI that was 1.2 times of the hyaluronic acid in mole and Sulfo-NHS that was 1.2 times of the hyaluronic acid in mole were added and stirred at room temperature for reaction for 30 min to obtain hyaluronic acid succinimide active ester; 500.0 mg human serum albumin lyophilized powder was dissolved in 10.0 mL sterile water and then added into the hyaluronic acid succinimide active ester; a pH value was adjusted to 7.0-7.2, and the mixture was stirred at room temperature for reaction for 60 min; then the mixture was added into a dialysis bag with a molecular weight up to 10000 after the reaction was finished, and unreacted reagent and reaction by-product were removed through dialysis; the hyaluronic acid-albumin solution after dialysis was lyophilized, and the lyophilized hyaluronic acid-albumin was dissolved in phosphate buffer (PBS buffer) with a pH of 5.5 to obtain albumin/hyaluronic acid solution;

(2) preparing taxol solution 50.0 mg taxol and 50.0 mg TPGS were dissolved in 1.0 mL mixture (9:1) of chloroform and ethyl alcohol to obtain the taxol solution;

(3) preparing taxol/TPGS/hyaluronic acid-albumin nanoformulation the taxol solution was added into the albumin/hyaluronic acid solution under a stirring condition to form initial emulsion; the initial emulsion was processed by a high-pressure homogenizer (9000-40000 psi) to obtain nanometre emulsion, the nanometre emulsion was transferred to a rotary evaporator to quickly remove organic solvent through reduced pressure and evaporation at 30.0-45.0☐, and the remaining was lyophilized under an aseptic condition to obtain lyophilized powder.

EMBODIMENT 13

Comparison of Drug Content of Targeted Nanoformulation 10.0 mg lyophilized matters of the nanoformulation obtained in embodiments 1 to 12 and references 1 to 2 were respectively added into 4.0 mL normal saline after aseptic filtration for redissolving, and then 2.0 mL of the mixture which was shaken evenly was filtered by a 0.22 μm filter. 2.0 ml chloroform-ethyl alcohol solution (9:1) was respectively added into the nanoformulation solution and sufficiently vibrated by a vortex oscillator to extract the drug in the preparation, the drug concentrations in the solution before and after being filtered were measured by a high pressure solution chromatography, and the drug contents and the drug yields in the multiple emulsions of the embodiments and references after removing the organic solvent were compared, wherein the drug content (%)=drug concentration*volume/(masses of drug and carrier)*100%, and the drug yield (%)=drug content/theoretical drug content*100%. The results were shown in Table 1

TABLE 1

Drug content and drug yield of the nanoformulation before being lyophilized, after being lyophilized and redissolved and after being redissolved and filtered

| Sample | Before being lyophilized | | Before being filtered | | After being filtered | |
|---|---|---|---|---|---|---|
| | Drug content/% | Drug yield/% | Drug content/% | Drug yield/% | Drug content/% | Drug yield/% |
| Embodiment 1 | 2.83 | 94.33 | 2.73 | 91.00 | 2.69 | 89.67 |
| Embodiment 2 | 6.66 | 95.14 | 6.46 | 92.29 | 6.35 | 90.71 |
| Embodiment 3 | 9.57 | 95.70 | 9.42 | 94.20 | 9.21 | 92.10 |
| Embodiment 4 | 9.76 | 97.60 | 9.56 | 95.60 | 9.31 | 93.10 |
| Embodiment 5 | 11.24 | 93.67 | 11.14 | 92.83 | 10.95 | 91.25 |
| Embodiment 6 | 14.09 | 93.93 | 13.68 | 91.20 | 13.46 | 89.73 |
| Embodiment 7 | 16.01 | 94.18 | 15.41 | 90.65 | 15.01 | 88.29 |
| Embodiment 8 | 18.79 | 93.95 | 18.18 | 90.90 | 17.43 | 87.15 |
| Embodiment 9 | 4.71 | 94.20 | 4.56 | 91.20 | 4.46 | 89.20 |
| Embodiment 10 | 6.44 | 92.00 | 6.32 | 90.29 | 5.96 | 85.14 |
| Embodiment 11 | 9.10 | 91.00 | 8.97 | 89.70 | 8.69 | 86.90 |
| Embodiment 12 | 11.27 | 93.92 | 10.80 | 90.00 | 10.43 | 86.92 |
| Reference 1 | 4.61 | 92.20 | 4.44 | 88.80 | 1.77 | 35.40 |
| Reference 2 | 4.76 | 95.20 | 4.58 | 91.60 | 2.61 | 52.20 |

It can be known from the results in Table 1 that the targeted nanoformulation of the present invention still had very high drug content and drug yield after being lyophilized and redissolved, and after being filtered by a 0.22 μm filter after being redissolved; the drug yield of the targeted nanoformulation in reference 1 and reference 2 before and after being lyophilized did not have great difference, but the drug yield after being filtered by the 0.22 μm filter was sharply reduced, which were only 39.86% and 56.99% before being filtered, indicating that more drug carrying particles were held back by a filter membrane in the filtering step, and the particle size of these particles should be larger than the aperture of the filter membrane of the 0.22 μm filter. However, there were only few particles with a particle size larger than 0.22 μm in the targeted nanoformulation of the present invention after being lyophilized and redissolved, which also indicated that the particle of the targeted nanoformulation of the present invention had good dispersibility, and was stable without aggregating. Therefore, the targeted nanoformulation still had high drug yield after being filtered.

EMBODIMENT 14

Figure 2:
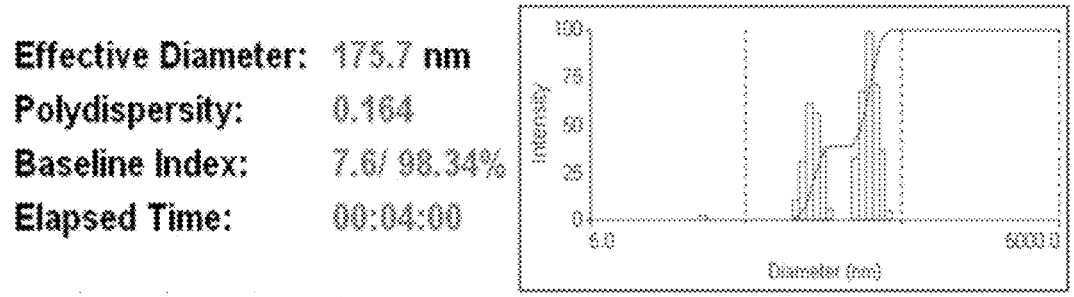
FIG. 2 is a particle size distribution diagram of a targeted nanoformulation particle before being filtered according to a reference 1.

Comparison of Particle Size of Targeted Nanoformulation 10.0 mg lyophilized matters of the nanoformulation obtained in embodiments 1 to 12 and references 1 to 2 were respectively added into 4.0 mL normal saline after aseptic filtration for redissolving, and then 2.0 mL of the mixture which was shaken evenly was filtered by a 0.22 μm filter. The particle size of the nanoformulation before and after being filtered was measured by an American Brookhaven laser light scattering granulometer (ZetaPALS), and the particle sizes in each embodiment after the organic solvent was removed (i.e., before being lyophilized) from the multiple emulsion were compared. The particle size distribution diagram of the targeted nanoformulation particle of the embodiment 3 before being filtered was shown in FIG. 1, the particle size distribution diagram of the targeted nanoformulation particle of reference 1 before being filtered was shown in FIG. 2, and all the results were shown in Table 2.

TABLE 2

Average particle size and particle size scope of the nanoformulation before being lyophilized, after being lyophilized and redissolved, and after being redissolved and filtered

| Sample | Before being lyophilized | | Before being filtered | | After being filtered | |
|---|---|---|---|---|---|---|
| | Average particle size/nm | Particle size scope/nm | Average particle size/nm | Particle size scope/nm | Average particle size/nm | Particle size scope/nm |
| Embodiment 1 | 146.1 | 73.2-182.9 | 149.8 | 78.6-192.8 | 147.0 | 78.6-178.5 |
| Embodiment 2 | 156.8 | 93.5-197 | 161.5 | 92.1-224.1 | 158.1 | 94.2-204.7 |
| Embodiment 3 | 157.4 | 91.3-202.5 | 163.2 | 90.0-220.4 | 159.4 | 91.5-200.2 |
| Embodiment 4 | 158.1 | 88.3-209.7 | 164.5 | 86.6-213.2 | 159.5 | 87.5-207.8 |
| Embodiment 5 | 156.5 | 81.9-216.5 | 161.0 | 84.3-219.6 | 157.7 | 82.2-214.0 |
| Embodiment 6 | 156.3 | 82.6-213.3 | 160.2 | 81.2-229 | 157.2 | 80.5-215.4 |
| Embodiment 7 | 160.4 | 87.6-210.9 | 174.3 | 92.3-232.1 | 169.5 | 88.7-216.2 |
| Embodiment 8 | 162.3 | 80.4-219.9 | 172.7 | 82.8-238.7 | 161.9 | 81.0-222.7 |
| Embodiment 9 | 162.5 | 85.5-217.3 | 167.8 | 77.9-241.2 | 164.2 | 78.1-214.5 |
| Embodiment 10 | 163.8 | 79.4-225.5 | 174.1 | 82.2-249.0 | 163.2 | 82.0-213.9 |
| Embodiment 11 | 160.8 | 80.8-215.7 | 170.1 | 82.0-236.5 | 161.6 | 80.5-211.6 |
| Embodiment 12 | 154.0 | 76.7-208.3 | 165.7 | 80.5-228.2 | 155.2 | 79.6-208.9 |
| Reference 1 | 129.4 | 48-226.9 | 175.7 | 57.8-342.1 | 154.7 | 51.1-205.0 |
| Reference 2 | 113.9 | 38.8-218.7 | 162.3 | 52.9-305.7 | 141.5 | 47.9-216.2 |

It could be known from the result in Table 2 that the particle size of the particle of the targeted nanoformulation in all embodiments before being lyophilized, and after being lyophilized and redissolved was different, the increase range of the particle size of the particle of the targeted nanoformulation according to the present invention after being lyophilized and redissolved was much smaller than that of the targeted nanoformulation in the reference; the particle size of the particle of the targeted nanoformulation of the present invention after being redissolved was not larger than 250 nm, and the maximum particle size of the particle of the targeted nanoformulation in the reference was close to 350 nm; and meanwhile, it could be discovered from the average particle size and the change of particle size scope before and after being redissolved that although the average particle size of the particle of the targeted nanoformulation in all embodiments and references was smaller than 220 nm, the particle size distribution scope of the reference was wider with many particles with the particle size larger than 220 nm, and the result was consistent with the result that the drug yield was lower after the targeted nanoformulation in the reference was redissolved and was filtered by 0.22 μm filter.

EMBODIMENT 15

Comparison of Stability of Targeted Nanoformulation (1) Comparison of Redissolving Stability Time 10.0 mg lyophilized matters of the nanoformulation obtained from embodiments 1 to 12 and references 1 to 2 were respectively redissolved by 4.0 mL normal saline subjected to aseptic filtration, then a suspension state, sediments and sediment appearing time were observed at room temperature. The results were shown in Table 3.

(2) Comparison of Stability of Binding Hydrophobic Drug with Albumin 50.0 mg lyophilized matters of the nanoformulation obtained from embodiments 1 to 12 and references 1 to 2 were placed in a dialysis bag with a cutoff molecular weight of 5000, disposed in 500.0 mL 37.0□ PBS buffer (0.01 M, containing 0.5 wt % Tween 80) with a pH of 7.4, and quantitative PBS buffer was taken timely and filtered by a 0.22 μm filtration membrane, and then measured by a high pressure solution chromatography. The results were shown in Table 3.

TABLE 3

Redissolving stability of nanoformulation and 24 h release rate

| Sample | 24 h release rate/% | Redissolving stability time/h |
|---|---|---|
| Embodiment 1 | 1.78 | >72 |
| Embodiment 2 | 2.26 | >72 |
| Embodiment 3 | 3.00 | >72 |
| Embodiment 4 | 3.23 | >72 |
| Embodiment 5 | 2.09 | >72 |
| Embodiment 6 | 2.05 | >72 |
| Embodiment 7 | 3.03 | >72 |
| Embodiment 8 | 3.99 | >72 |
| Embodiment 9 | 2.84 | >72 |
| Embodiment 10 | 4.21 | >72 |
| Embodiment 11 | 3.44 | >72 |
| Embodiment 12 | 4.08 | >72 |
| Reference 1 | 21.35 | 60 |
| Reference 2 | 19.29 | 48 |

It could be known from Table 3 that only no more than 5.00% of the targeted nanoformulation of the present invention was released in the PBS buffer in 24 h, which was much lower than that of the references, indicating that the binding force between the drug and the carrier was relatively strong, which was more beneficial for avoiding or reducing the drug leaked from the carrier in the operating process before the drug circulated in the body and reached the targeted site, thereby reducing the drug toxicity, increasing the utilization ratio of the drug, and being beneficial for reducing the dosage of administration. It could be known from the redissolving dispersion stability time that the targeted nanoformulation particle of the present invention had good dispersity and weak aggregating tendency, and the results were consistent with the results that the particle sizes of the particles before and after being redissolved were not obviously increased.

EMBODIMENT 16

Animal Experiment (1) Tumor Suppression Experiment

BALB/c naked mice were used to construct a human MX-1 breast cancer cell tumor-bearing mouse model, the mice were randomly divided into a tumor-bearing mouse negative group and a group of embodiments 1 to 2, a group of embodiments 5 to 6 and a group of references 1 to 2 when the tumor grown to 150-300mm³h, and each group had six mice. 10.0 mg/kg drug was injected in a caudal vein once in every five days and continuously injected for five times, and the tumor volume was measured once in every five days in the experiment process, wherein a volume calculation method was as follows: $V=d^2D/2$, where d was the length in a short direction, and D was the length in a long direction. The results were shown in FIG. 3.

Figure 3:
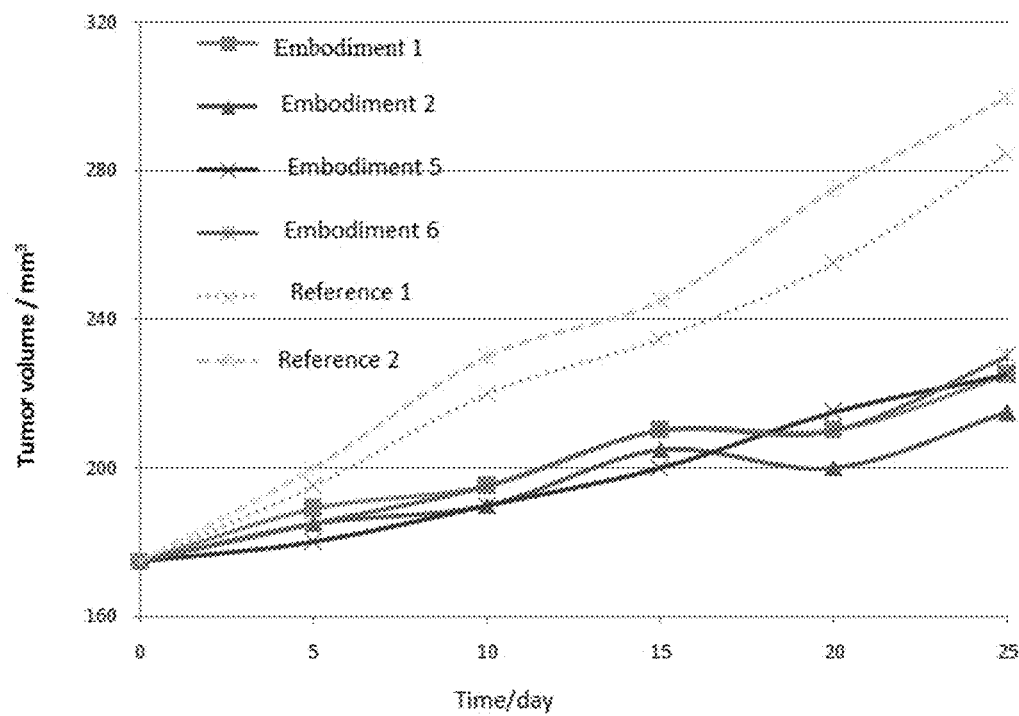

It could be known from FIG. 3 that the targeted nanoformulation of the present invention had more obvious inhibiting effect on tumor with the same concentration, indicating that the utilization ratio of the drug of the targeted nanoformulation of the present invention was higher.

(2) Comparison of Drug Distribution in Mice

The distribution of the taxol targeted nanoformulation in vivo was measured by using the taxol marked by $^{14}C$. 5.0 mg/mL taxol targeted nanoformulations of the embodiment 1, embodiment 6 and references 1 to 2 were injected into the mice which was already inoculated with an H22 tumor cell for 7 days through the caudal vein. The injected mice were put to death in 24 h, the viscera and the tumors were respectively taken out to measure the intensity of radioactivity thereof, and the concentration of the taxol in each tissue was calculated. The results were shown in FIG. 4.

Figure 4:
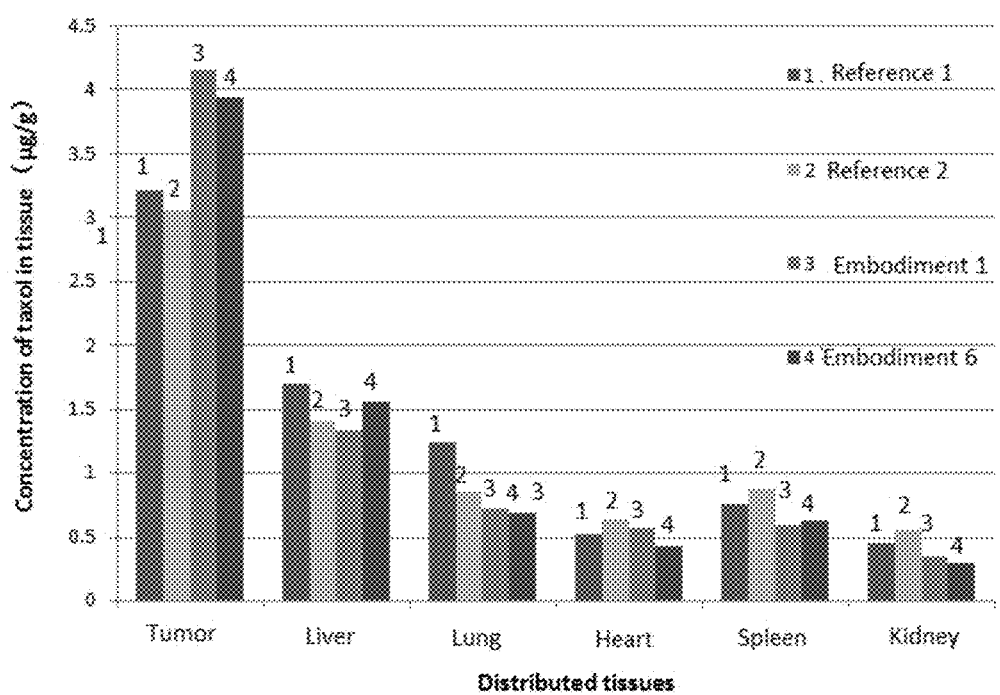
FIG. 4 is a comparison diagram of a biological targeting property of targeted nanoformulations according to embodiment 1, embodiment 6 and references 1 to 2.

It could be known from FIG. 4 that the targeted nanoformulation of the present invention was distributed in various tissues in the body after intravenous injection, but being compared with the references, the accumulation of the drug carrying particle of the present invention in the tumor was obviously increased, but the accumulation in other issues was relatively reduced, which was consistent with the above inhibiting effect on tumor, thus indicating that the toxicity of the targeted nanoformulation of the present invention was relatively low when being compared with the references, which was beneficial for reducing the side effects and increasing the compliance of patients.

The technical features of the above-described embodiments may be combined arbitrarily. To make the description succinct, all the possible combinations of the technical features in the above embodiments are not described. However, all the combinations of these technical features shall be deemed as falling within the scope recorded in the description as long as there are no contradictions in the combinations of these technical features The above described embodiments merely represent several embodiments of the invention, and the description thereof is more specific and detailed, but it should not be understood as a limitation to the patent scope of the invention. It should be noted that those skilled in the art may make a plurality of deformations and improvements without departing from the concept of the invention, and these deformations and improvements shall all fall within the protection scope of the invention. Therefore, the protection scope of the invention shall be subject to the claims appended.

The invention claimed is:

1. A targeted hydrophobic anti-tumor drug nanoformulation, comprising a hydrophobic anti-tumor drug and a carrier with a mass ratio of 1:4 to 1:32.5, wherein the carrier is composed of 37.5-95.3 wt% unmodified albumin and 4.7-62.5 wt% hyaluronic acid-albumin conjugate, a molar ratio of albumin and hyaluronic acid in the hyaluronic acid-albumin conjugate is 1:1 to 1:20, and the hydrophobic anti-tumor drug is selected from taxol, docetaxel, aziditaxel, adriamycin, camptothecin, vancomycin, thiotepa or their derivatives thereof.

2. The targeted hydrophobic anti-tumor drug nanoformulation according to claim 1, comprising a hydrophobic anti-tumor drug and a carrier with a mass ratio of 1:4.8 to 1:19, wherein the carrier is composed of 50.0-95.0 wt% unmodified albumin and 5.0-50.0 wt% hyaluronic acid-albumin conjugate, a molar ratio of albumin and hyaluronic acid in the hyaluronic acid-albumin conjugate is 1:1 to 1:20, and the hydrophobic anti-tumor drug is selected from taxol, docetaxel, aziditaxel, adriamycin, camptothecin, vancomycin, thiotepa or their derivatives thereof.

3. The targeted hydrophobic anti-tumor drug nanoformulation according to claim 2, wherein the molecular weight of the hyaluronic acid is 2-60 kDa.

4. The targeted hydrophobic anti-tumor drug nanoformulation according to claim 2, wherein the unmodified albumin is selected from human serum albumin, bovine serum albumin, egg albumin and recombinant human serum albumin, and the albumin constituting the hyaluronic acid-albumin conjugate is selected from human serum albumin, bovine serum albumin, egg albumin and recombinant human serum albumin.

5. The targeted hydrophobic anti-tumor drug nanoformulation according to claim 2, further comprising a nanoparticle stabilizer, wherein the nanoparticle stabilizer is selected from polyoxyethylene-polypropylene oxide-polyoxyethylene block polymer, d-α-tocopheryl polyethylene glycol succinate and povidone, and the nanoparticle stabilizer is 1.0-10.0% of the mass of the hydrophobic anti-tumor drug.

6. The targeted hydrophobic anti-tumor drug nanoformulation according to claim 1, wherein the molecular weight of the hyaluronic acid is 2-60 kDa.

7. The targeted hydrophobic anti-tumor drug nanoformulation according to claim 1, wherein the unmodified albumin is selected from human serum albumin, bovine serum albumin, egg albumin and recombinant human serum albumin, and the albumin constituting the hyaluronic acid-albumin conjugate is selected from human serum albumin, bovine serum albumin, egg albumin and recombinant human serum albumin.

8. The targeted hydrophobic anti-tumor drug nanoformulation according to claim 1, further comprising a nanoparticle stabilizer, wherein the nanoparticle stabilizer is selected from polyoxyethylene-polypropylene oxide-polyoxyethylene block polymer, d-α-tocopheryl polyethylene glycol succinate and povidone, and the nanoparticle stabilizer is 1.0-10.0% of the mass of the hydrophobic anti-tumor drug.

9. A preparation method of the targeted hydrophobic anti-tumor drug nanoformulation according to claim 1, comprising:

(1) preparing hyaluronic acid-albumin conjugate:
adding hyaluronic acid and albumin into an aqueous medium for dissolution, adjusting a solution pH to 5.0-6.0, adding N-(3-Dimethylaminopropyl)-N'-ethylcarbodiimide hydrochloride and N-hydroxysulfosuccinimide sodium salt into the above solution for reaction for 15-60 min, then adjusting the solution pH to 7.0-7.5, continuously stirring at room temperature for reaction for 3-24 h, dialyzing to remove unbound hyaluronic acid, unreacted N-(3-Dimethylaminopropyl)-N'-ethylcarbodiimide hydrochloride, N-hydroxysulfosuccinimide sodium salt and other by-products after the reaction is finished, and obtaining the hyaluronic acid-albumin conjugate after being lyophilization; or dissolving the hyaluronic acid into an aqueous medium, adjusting a solution pH to 5.0-6.0, adding N-(3-DimethylaminopropyL)-N'-ethylcarbodiimide hydrochloride and N-hydroxysulfosuccinimide sodium salt, stirring at room temperature for reaction for 15-60 min to obtain hyaluronic acid succinimide active ester; and then adding the hyaluronic acid succinimide active ester drop by drop into an albumin aqueous solution or adding the albumin aqueous solution drop by drop into the hyaluronic acid succinimide active ester, adjusting the solution pH to 7.0-7.5, stirring at room temperature for reaction for 3-24 h, dialyzing to remove unbound hyaluronic acid, unreacted N-(3-Dimethylaminopropyl)-N'-ethylcarbodiimide hydrochloride, N-hydroxysulfosuccinimide sodium salt and other by-products after the reaction is finished, and obtaining the hyaluronic acid-albumin conjugate after being lyophilized;

(2) formulating carrier solution:

dissolving [the] unmodified albumin and the hyaluronic acid-albumin conjugate prepared in step (1) into an aqueous medium to obtain a carrier solution;

(3) formulating drug solution:

dissolving a hydrophobic anti-tumor drug, or a hydrophobic anti-tumor drug and a nanoparticle stabilizer into an organic solvent to obtain a drug solution; and (4) preparing nanoformulation:

adding the drug solution prepared in step (3) into the carrier solution prepared in step (2) under homogenization condition to obtain initial emulsion, obtaining multiple emulsion under high-pressure homogenization condition, then removing the organic solvent, filtering, and lyophilizing to obtain the targeted hydrophobic anti-tumor drug nanoformulation.

10. The preparation method of the targeted hydrophobic anti-tumor drug nanoformulation according to claim 9, wherein the concentration of the carrier in the carrier solution according to step (2) is 4.0-50.0 mg/mL, and the concentration of the hydrophobic anti-tumor drug in the drug solution according to step (3) is 16.0-345.0 mg/m L.

11. The preparation method of the targeted hydrophobic anti-tumor drug nanoformulation according to claim 9, wherein the aqueous medium according to step (1) is 2-(N-morpholine) ethanesulfonic acid buffer, phosphate buffer or sterile water; the aqueous medium according to step (2) is sterile water, phosphate buffer, normal saline, 5.0 wt% aqueous glucose solution or 5.0 wt% mannitol solution; and the organic solvent according to step (3) is dichloromethane, chloroform, a mixture of dichloromethane and ethyl alcohol, or a mixture of chloroform and ethyl alcohol.

12. The preparation method of the targeted hydrophobic anti-tumor drug nanoformulation according to claim 9, the pressure of the high-pressure homogenization condition according to step (4) is 10000-40000 psi, the material flow of the high-pressure homogenization condition is 10.0-25.0 L/h, and the cycle index of the high-pressure homogenization condition is 7-20; and the method of removing the organic solvent is to remove the organic solvent by reduced pressure and rotary evaporation under a condition of 15.0-45.0° C.

* * * * *